United States Patent [19]

Eibl et al.

[11] Patent Number: 5,770,199
[45] Date of Patent: Jun. 23, 1998

[54] METHOD FOR VIRUS INACTIVATION IN THE PRESENCE OF POLYALKYLENE GLYCOL AS WELL AS THE PHARMACEUTICAL PREPARATION OBTAINED THEREWITH

[75] Inventors: Johann Eibl; Friedrich Dorner, both of Vienna; Noel Barrett, Klosterneuburg/Weidling, all of Austria

[73] Assignee: Immuno Aktiengesellschaft, Vienna, Austria

[21] Appl. No.: 624,516

[22] PCT Filed: Jan. 10, 1995

[86] PCT No.: PCT/IB95/00019

§ 371 Date: Jun. 28, 1996

§ 102(e) Date: Jun. 28, 1996

[87] PCT Pub. No.: WO95/09657

PCT Pub. Date: Apr. 13, 1995

[30] Foreign Application Priority Data

Oct. 6, 1993 [DE] Germany .......................... 43 34 087.3
Sep. 27, 1994 [DE] Germany .......................... 44 34 538.0

[51] Int. Cl.⁶ .......................... A61K 39/395; A61K 35/16
[52] U.S. Cl. .......................... 424/176.1; 424/530; 514/2; 514/723; 514/772; 530/380; 530/381; 530/382; 530/383; 530/384; 530/387.1; 530/390.1; 530/830
[58] Field of Search .......................... 424/176.1, 530; 514/1, 2, 723, 722; 530/380, 381, 382, 383, 384, 387.1, 390.1, 830

[56] References Cited

U.S. PATENT DOCUMENTS

| | | | |
|---|---|---|---|
| 2,232,820 | 2/1941 | Brouse | 221/95 |
| 2,232,821 | 2/1941 | Brown et al. | 188/5 |
| 2,303,432 | 12/1942 | Brown | 99/123 |
| 2,380,166 | 7/1945 | Griffin | 252/311.5 |
| 4,069,216 | 1/1978 | Shanbrom | 260/112 B |
| 4,315,919 | 2/1982 | Shanbrom | 424/177 |
| 4,481,189 | 11/1984 | Prince | 424/101 |
| 4,721,777 | 1/1988 | Uemura | 530/389 |
| 4,727,027 | 2/1988 | Wiesehahn et al. | 435/173 |
| 4,764,369 | 8/1988 | Neurath et al. | 424/89 |
| 5,055,557 | 10/1991 | Zimmerman | 530/381 |
| 5,132,406 | 7/1992 | Uemura et al. | 530/390.1 |

FOREIGN PATENT DOCUMENTS

| | | |
|---|---|---|
| 0 050 061 | 4/1982 | European Pat. Off. . |
| 0 083 999 | 7/1983 | European Pat. Off. . |
| 0 099 445 | 2/1984 | European Pat. Off. . |
| 0 124 506 | 11/1984 | European Pat. Off. . |
| 0 177 836 | 4/1986 | European Pat. Off. . |
| 0 292 003 | 11/1988 | European Pat. Off. . |
| 0 399 321 | 11/1990 | European Pat. Off. . |
| 0 479 597 | 4/1992 | European Pat. Off. . |
| 0 530 173 | 3/1993 | European Pat. Off. . |
| 2 339 621 | 8/1977 | France . |
| 44 34 538 | 4/1995 | Germany . |
| 90/07524 | 7/1990 | WIPO . |
| 90/15613 | 12/1990 | WIPO . |

*Primary Examiner*—C. Warren Ivy
*Assistant Examiner*—Evelyn Huang
*Attorney, Agent, or Firm*—Foley & Lardner

[57] ABSTRACT

The invention relates to a pharmaceutical preparation comprising a plasma protein wherein said preparation is free of infectious agents as well as essentially free of denaturation products and is obtainable by a method that encompasses the following steps:

a) addition of a polyether and a chaotropic agent to a solution comprising the plasma protein, optional lyophilization of the solution;

b) inactivation of infectious agents in the presence of the polyether by a physio-chemical or chemical treatment, and c) removal of the polyether and the chaotropic agent.

23 Claims, No Drawings

METHOD FOR VIRUS INACTIVATION IN THE PRESENCE OF POLYALKYLENE GLYCOL AS WELL AS THE PHARMACEUTICAL PREPARATION OBTAINED THEREWITH

DESCRIPTION

This application is the national phase of PCT/EP94/03298, field Oct. 6, 1994, issued as WO95/09657 on Apr. 13, 1995.

The invention relates to a pharmaceutical preparation comprising a plasma protein which is obtainable by a highly effective method for the inactivation of infectious agents under maintenance of the biological activity.

The invention also encompasses a method for the production of the mentioned pharmaceutical preparation which inactivates detectable, potentially present viruses.

BACKGROUND OF THE INVENTION

Plasma proteins are proteins which can be obtained from human or animal blood and/or plasma. The plasma proteins are intended for pharmaceutical preparations for therapeutic, prophylactic or diagnostic use. Such preparations can contain enzymes, proenzymes including coagulation factors, enzyme cofactors, enzyme inhibitors, immunoglobulins, albumin, plasminogen, fibrinogen, fibronectin, t-PA, urokinase, prourokinase or plasma. Recombinant polypeptides, which are equivalent to the mentioned plasma proteins based on their properties, are also understood as plasma proteins.

Pharmaceutically applicable preparations which are of biological origin, i.e. are obtained from natural sources or cell cultures and/or are produced recombinantly, are understood as biological preparations.

However, immunoglobulin preparations, monoclonal antibodies or fragments thereof, supernatants from cell cultures and ascites fluid from mice are also numbered among biological preparations.

An infection risk from potentially present agents such as hepatitis or AIDS viruses exists with the administration of a biological preparation, especially a plasma protein containing preparation. Therefore, the method of preparation of these preparations must encompass suitable inactivation measures.

Pathogenic agents which can be transferred from one organism to another organism, for example viruses or prions, are understood as infectious agents.

Extensive literature is known which deals with the inactivation of infectious agents in pharmaceutical preparations.

The heating of plasma proteins in solution is one of the most effective methods for inactivation of viruses. It is known that a virus-safe albumin containing preparation can be produced by heating an aqueous albumin solution at a temperature of 60° C. for 10 hours. The biological activity of the albumin is not adversely influenced therewith since albumin is a relatively stable plasma protein.

An increase of the virus inactivation capability of a heat treatment of blood products in solution by the addition of ammonium sulfate is known in the art (EP 124 506). Thereby, the problem of simultaneous inactivation of plasma proteins is known and for this reason it is proposed to add protein stabilizing substances such as glycine. However, a desired stabilization of the plasma proteins simultaneously signifies an undesired stabilization of the infectious agents. Hence, the attempt is to exclude infectiousness of the preparation, and simultaneously, to considerably maintain its biological activity.

Addition of stabilizers to plasma protein containing solutions is known for example from EP 292 003. Saccharides or sugar alcohols and neutral salts such as acetates, phosphates and sulfates are added as stabilizers. Here, salts have a stabilizing effect.

A virus inactivating effect of salts is also described in WO 90/07524. Antibodies against protein C are stable at 22° C. for at least 2 hours in the presence of at least 2.6M guanidine or 2M calcium thiocyanate. Such a treatment is also proposed in order to inactivate potentially present viruses. Due to their chaotropic behavior, the compounds mentioned have an inactivating effect not only with respect to viruses, but also with respect to proteins. Therefore, it is important that the antibodies can be incubated with these compounds for a certain time at room temperature with these compounds without loosing their affinity to protein C.

A method for the inactivation of viruses by addition of sodium thiocyanate to plasma protein containing solutions is known from WO 90/15613. In order not to denature the plasma protein, the treatment is carried out at 4° C. and during a short treatment period.

Additionally, thiocyanates were used as elution agents in the course of immunaffinity chromatography. Subsequent to the elution, the removal of the thiocyanate occurs immediately in order to prevent damage to the purified proteins (see U.S. Pat. No. 5,055,557).

SUMMARY OF THE INVENTION

An object of the present invention is to make a pharmaceutical preparation comprising a plasma protein available which, as a result of its method of production, is free from infectious agents as well as considerably free from denaturation products.

The above object is achieved according to the invention by a pharmaceutical preparation comprising a plasma protein which is obtainable by a method which encompasses the following steps:

a) addition of a polyether to a solution comprising the plasma protein, optional lyophilization of the solution;
b) inactivation of infectious agents in the presence of the polyether by a physio-chemical or chemical treatment, and
c) removal of the polyether.

According to the invention, polyethers also encompass polyhydroxyethers such as polyalkylene glycol, and especially polyethylene glycol and polypropylene glycol.

A preferred embodiment is characterized in that the inactivation of infectious agents in step (b) is carried out in the presence of the polyether and a chaotropic agent and the polyether and the chaotropic agent are removed in step (c).

A further preferred embodiment is characterized in that in step (a) the polymer is a low molecular polyethylene glycol selected from the group consisting of PEG 200, PEG 300, PEG 400, PEG 600, PEG 900 and PEG 1000, (b) the inactivation of infectious agents is carried out in the presence of the polyethylene glycol, and (c) the polyethylene glycol is removed.

In a further preferred embodiment, the inactivation of infectious agents in step (b) occurs in the presence of the polyether by a physical, physio-chemical or chemical treatment with the proviso that a detergent treatment is excluded.

In accomplishing this and other objects, there is provided, in accordance with one aspect of the present invention, a pharmaceutical preparation comprising a plasma protein that is at least substantially free of infectious agents and denaturation products, wherein the plasma protein is obtainable by the steps of contacting a solution comprising a plasma protein with a polyether to inactivate any contaminating infectious agents, including viruses, by physico-chemical or chemical treatments, and removing the polyether to ultimately obtain the protein. The polyether can be added to the solution comprising the plasma protein, and the inactivation conducted. Heat, irradiation and virucidal agents also can be employed. Prior to conducting the inactivation step, the solution can be lyophilized. Additionally, a chaotropic agent can be added to the solution along with the polyether.

In accordance with another aspect of the present invention, there is provided a method of producing a pharmaceutical preparation that is at least substantially free of infectious agents, comprising the steps of contacting a solution comprising a plasma protein with a polyether to inactivate any contaminating infectious agents, including viruses, by physico-chemical or chemical treatments, and removing the polyether to ultimately obtain the protein. The polyether can be added to the solution comprising the plasma protein, and the inactivation conducted. Heat, irradiation and virucidal agents also can be employed. Additionally, a chaotropic agent can be added to the solution along with the polyether.

Prior to conducting the inactivation step, the solution can be lyophilized. The method is preferably conducted at a temperature of 20° C. to 60° C. for 1 to 10 hours. Chromatographic steps, such as HPLC, can be used according to the present invention to remove denaturation products from the solution containing the plasma proteins.

As stated above, a chaotropic agent can be added to the solution along with the polyether. The chaotropic agents have been found to have a synergistic effect with the polyether in the viral inactivation process. Preferred chaotropic agents include thiocyanates, urea and guanidinium salts. Preferred thiocyanates include ammonium thiocyanate, sodium thiocyanate and calcium thiocyanate. Preferred guanidinium salts include guanidinium hydrochloride. The chaotropic agent is preferably used at a concentration of 0.1 to 2M.

Preferably, the polyether is added at a concentration of about 5 to 30 percent and other suitable concentration so that the protein does not precipitate. The polyether can be a polyhydroxyether, such as polyalkylene glycol. Preferred polyalkylene glycols include polyethylene glycol and polypropylene glycol. Preferred polyethylene glycols includes low molecular weight molecules, such as PEG 200, PEG 300, PEG 400, PEG 600, PEG 900 and PEG 1000.

The present invention is adaptable to obtaining any type of plasma protein, including those proteins involved in causing or inhibiting coagulation, fibrinolysis, and/or thrombolysis. Immunoglobulins can also be obtained according to the present invention. According to the present invention, at least 50%, more preferably at least 80% and most preferably at least 90% of the biological activity of the plasma protein is retained after practice of the present invention.

DETAILED DESCRIPTION OF PREFERRED EMBODIMENTS

It was surprisingly found that the addition of a polyether, such as for example polyethylene glycol, at a concentration of 5 to 30 percent by weight, has an unexpectedly positive effect on an inactivation treatment for the elimination of infectiousness. Thereby, the conditions of the inactivation treatment can be selected in such a manner that the biological activity of the plasma proteins is considerably maintained.

The concentration of the polyether is selected in such a manner that no precipitation reactions are caused. It should already be mentioned here that, with the addition of chaotropic agents as well, the treatment is preferably carried out such that proteins are not precipitated. Namely, the precipitation of proteins might cause the risk that infectious particles are included in the precipitate. Thereby, the infectious particles are made poorly accessible to an inactivation treatment. Thus, in the absence of a precipitate, no delayed inactivation of infectious agents is to be observed. Also, it is possible to reduce the temperature of a heat treatment with the same effectiveness.

The improved inactivation treatment in the presence of a polyether could not be expected. Namely, it was found for the first time that viruses are inactivated in the presence of a polyether alone, for example polyethylene glycol.

The treatment for inactivation of infectious agents preferably encompasses a heat treatment, especially at a temperature of 20° to 60° C., preferably in the range of 25° to 45° C.

Preferably, polyethylene glycol, and particularly preferably a low molecular polyethylene glycol, is used as a suitable polyether. Here, such particularly suitable polyethylene glycols are selected from the group consisting of PEG 200, PEG 300, PEG 400, PEG 600, PEG 900 and PEG 1000. A number of known measures are suitable for the removal of the polyether. The plasma protein is removed from the treated solution preferably by precipitation or adsorption, preferably by chromatography. The polyether further remains in solution and is thus separated from the plasma protein. The polyether is removed completely and/or to a physiologically acceptable amount in the preparation ready for administration.

According to the invention, a solution containing the plasma protein may be lyophilized after addition of a polyether and the subsequent treatment of the plasma protein for inactivation of infectious agents is conducted in the presence of the polyether in the solid state being a lyophilisate. This treatment constitutes a physio-chemical or chemical treatment. For this purpose, a treatment in the presence of virucide substances, optionally combined with an irradiation treatment or heat treatment, is also considered.

According to a preferred embodiment, the inactivation of infectious agents is effected by treatment of a solution or lyophilisate of the preparation in the presence of an additional chaotropic agent. It has been determined that a synergistic effect on the inactivation of viruses is observed by the combination of a chaotropically effective salt, such as for example thiocyanate, with a polyether, such as for example polyethylene glycol, wherein the biological activity of the preparation is essentially maintained. Thus, resistant viruses such as vaccinia virus or parvovirus are also substantially inactivated more quickly and at smaller concentrations of thiocyanate in comparison to a treatment with thiocyanate alone. The reduction of the thiocyanate concentration and the treatment duration results in a preferable effect of the biological activity of the preparation.

As a chaotropic agent, a thiocyanate, urea or guanidinium salt is used for example. Sodium, ammonium or calcium thiocyanate are particularly suitable. Guanidinium hydrochloride is most preferred as a guanidinium salt.

The chaotropic agents are used in concentrations of approximately 0.1 to 2M. Also here, as discussed above, the treatment is carried out in the presence of additional chaotropic salts under conditions in which proteins are not precipitated.

With the method according to the invention, it is for the first time possible to treat labile proteins, i.e. proteins which are easily denatured, in the presence of chaotropic salts in solution while essentially maintaining the biological activity of the plasma proteins.

Thus, the addition of a polyether during virus inactivation permits the production of a pharmaceutical preparation which comprises plasma proteins that are considerably free of denaturation products.

The removal of the chaotropic agent to an amount which does not adversely influence the physiological tolerance of the preparation is done in a known manner. Preferably, this amount should lie under the detection limit. For removal of the chaotropically effective salts, the plasma protein containing solution can be dialyzed and/or ultrafiltered. Simultaneous with this physical treatment, potentially present infectious particles are separated. On the other hand, the plasma protein can be separated from the chaotropic agents by precipitation and/or adsorption techniques, preferably by chromatography.

In one of the above mentioned suitable embodiments according to the invention a detergent treatment is excluded in step (b); such a detergent treatment is understood as a treatment with a detergent usually used for virus inactivation according to the art, i.e. with tensides such as surface active agents used for such purposes, especially for example polyoxyethylene derivatives of sorbitan esters (polysorbate) which are obtainable under the trademark "Tween". Such detergents, in connection with a virus inactivation or at least in combination with other measures, are described for example in EP-A-479597 (where Tween 80 is especially used), U.S. Pat. No. 4,764,369 (according to which the virus inactivation is carried out with di- or trialkyl phosphate in combination with detergents) and EP-B-0050061 (wherein the virus inactivation and reduction, elimination, removal or partitioning of substances which possess undesired effects, for example pyrogenicity, occurs by addition of an amphiphilic agent that is a cholic acid salt, for example selected from sodium cholate and sodium deoxycholate or a non-ionic tenside selected from the polyoxyethylated derivatives of partial esters of $C_{12}$–$C_{22}$ fatty acids and anhydrides).

In particular, detergents to be excluded according to the invention are:

non-ionic detergents, polyoxyethylene derivatives of fatty acids, partial esters of sorbit(ol) anhydrides such as "Tween 80", "Tween 20" and "Polysorbate 80" and non-ionic oil soluble detergents as sold under the trademark "Triton X-100" (oxyethylated alkylphenol) as well as sodium deoxycholate and so-called "zwittergents", i.e. synthetic zwitterionic detergents which are known as "Sulfobetaine" such as N-dodecyl-N,N-dimethyl-2-ammonio-1-ethane sulfonate, and similar substances or non-ionic detergents such as octyl-beta-D-glucopyranoside.

In general, the detergents are non-ionic surface active oxyethylated alkylphenols, polyoxyethylene sorbitan fatty acid esters, polyoxyethylene acids and polyoxyethylene oxypropylene fatty acids. Specific examples thereof are the following:
alkylphenoxypolyethoxy (30) ethanol
polyoxyethylene (2) sorbitan monolaurate
polyoxyethylene (20) sorbitan monopalmitate
polyoxyethylene (20) sorbitan monostearate
polyoxyethylene (20) sorbitan tristearate
polyoxyethylene (20) sorbitan monooleate
polyoxyethylene (20) sorbitan trioleate
polyoxyethylene (20) palmitate
polyoxyethylene (20) laurylether
polyoxyethylene (20) cetylether
polyoxyethylene (20) stearylether
polyoxyethylene (20) oleylether
polyoxyethylene (20) hydrated castor oil
polyoxyethylene (20) oxypropylene monostearate Amphiphilic surface active agents which contain hydrophilic water soluble as well as hydrophobic water insoluble groups and which are usually classified in anionic, cationic, ampholytic and non-ionic surface active agents; examples for such amphiphilic detergents excluded according to the invention are:
anionic agent:
sulfated oxyethylated alkylphenol (Triton W-30®);
sulfated laurylether alcohol;
sodium dodecylbenzol sulfonate (Nacconol NR®);
sodium 2-sulfoethyloleate (Igepon A®);
sodium N-methyl-N-oleylethanol sulfonate (Igepon T®);
sodium dodecyl sulfate;
sodium cholate;
sodium deoxycholate;
sodium dodecyl sulfonate;
sodium dodecyl-N-sarconisate.
Cationic agent:
dodecyldimethylbenzylamminium chloride (Triton K-60®);
oxyethylated amines (Ethomeen®);
cetyltrimethylamminium bromide;
tetradecylammonium bromide;
dodecylpyrimidinium chloride;
hexadecyltrimethylammonium chloride.
Ampholytic agent:
dodecyl beta-alanine;
N-dodecylaminoethane sulfonic acid;
palmitoyllysolecithin;
dodecyl-N-betaine.

Oxyethylated alkylphenols (Triton X-100®), partial esters of $C_{12}$–$C_{22}$ fatty acids (for example, lauric, palmitic, stearic and oleic acids) and hexite anhydrides (for example, hexitans and hexides) (Spans) such as they are described in U.S. Pat. Nos. 2,232,820, 2,232,821 and 2,303,432; polyoxyethylated derivatives of these partial esters which are obtained by addition of polyoxyethylene chains on nonesterified hydroxyl groups (Tween®, for example Tween 80® or Polysorbate 80®) such as described in U.S. Pat. No. 2,380,166; partial polyoxyethylated fatty acids (Myrj 45®) and polyoxyethylene fatty acid alcohol ester (Brij®).

Among the excluded oxyethylated alkylphenols (Triton X), those of the formula $RC_6H_4(OC_2H_4)_nOH$ wherein R is octyl or nonyl and n means at least 3, such as octylphenoxyethanol for example are to be especially named; such surface active agents are sold under the trademark "Triton X", for example Triton X-100, Triton X-165, Triton X-205, Triton X-305, Triton X-405 and Triton N-100.

Further detergents which are excluded from the suitable embodiments according to the invention are the amphiphilic detergents: cholic acid salts such as sodium cholate and sodium dexycholate.

Above all, the pharmaceutical preparation according to the invention surprisingly is characterized by a very small degree of denaturation. The biological activity of the plasma protein after inactivation of infectious agents is—in comparison to the activity before the inactivation treatment—maintained to at least 50%, preferably at least 80%, and most preferably 90%.

In case of a factor of coagulation, fibrinolysis or thrombolysis or its derivative, the biological activity of the preparation according to the invention is measured by its influence on the enzymatic reaction in the course of blood coagulation. The biological activity of an immunoglobulin can be estimated after the separation of the preparation by means of HPLC chromatography. Any possible denaturation products and/or aggregates are thereby separated from immunoglobulin monomers and/or dimers and can be quantitatively determined.

The positive effect on the inactivation of infectious agents by polyethers, such as polyethylene glycol, was surprising for the skilled expert. It was generally known that substances which stabilize plasma proteins also have a stabilizing effect on viruses. Reference is made to a publication from B. Horowitz et al. in Transfusion, 25, 523–527 (1985). According to this, worse inactivation kinetics were to be expected in the presence of polyethers.

The method according to the invention is carried out for a period which enables that the potentially present viruses from the group consisting of the large membrane coated RNA viruses, small membrane coated RNA viruses and membrane coated DNA viruses are completely inactivated. This can be confirmed by tests using model viruses. The conditions of the method according to the invention are selected in such a manner that a virus from each group added to the biological preparation is inactivated by the method according to the invention to a virus titer which is under the detection limit. Above all, HIV, FSME virus and pseudorabies virus (PSR) are suitable as model viruses.

The method according to the invention is especially suitable for the inactivation of hepatitis viruses, above all hepatitis B, hepatitis C and non-A, non-B hepatitis viruses as well as retroviruses, above all AIDS viruses.

The invention is more closely illustrated by the following Examples:

1. Inactivation of model viruses in a gammaglobulin containing solution with thiocyanate in the presence of polyethylene glycol A 10 percent solution containing an i.m. gammaglobulin was produced by plasma fractionation according to Cohn. The solution was mixed with a suspension containing HIV-1, FSME virus or PSR virus. Ammonium thiocyanate up to a concentration of 0.3M and PEG 200 up to an amount of 10 percent by weight was added to the solution. Subsequently, the solution was heated to 30° C. and the respective virus titer was determined after 0, 1, 3, 6 and 10 hours. The results are given in the following Table. The virus titer in the original virus suspension served as a control value. The virus titer at the time of the treatment time 0 is given in the tables in each case.

By means of HPLC, it could be established that no aggregation resulted through the inactivation treatment.

TABLE 1

|  | control | 0 | 1 | 3 | 6 | 10 |
|---|---|---|---|---|---|---|
| HIV-1 | $10^{7.9}$ | $10^{2.1}$ | $\leq 10^{0.5}$ | $\leq 10^{0.5}$ | $\leq 10^{0.5}$ | $\leq 10^{0.5}$ |
| FSME | $10^{7.5}$ | $10^{2.9}$ | $10^{0.6}$ | $<10^{0}$ | $<10^{0}$ | $<10^{0}$ |
| PSR | $10^{7.9}$ | $10^{5.6}$ | $\leq 10^{0.5}$ | $\leq 10^{0.5}$ | $\leq 10^{0.5}$ | $\leq 10^{0.5}$ |

Time (h) spans columns 0 through 10.

2. Comparative example each with ammonium thiocyanate or polyethylene glycol only Ammonium thiocyanate at a concentration of 0.3M was added to the gammaglobulin containing solution of Example 1. In parallel, PEG 200 up to an amount of 10 or 30 percent was added to the gammaglobulin containing solution of Example 1. The solutions were mixed with an HIV-1 containing suspension and held at a temperature of 30° C. The virus titer was measured at 0, 0.5, 1, 1.5, 2, 3, 6, and 10 hours. The results are given in the following Table.

TABLE 2

|  | Virus titer treatment period (h) | | | | | | | |
|---|---|---|---|---|---|---|---|---|
|  | control | 0 | 1 | 1.5 | 2 | 3 | 6 | 10 |
| PEG 10% | $10^{7.4}$ | $10^{6.1}$ | $10^{6.5}$ | n.d. | n.d. | $10^{6.2}$ | $10^{5.9}$ | $10^{5.7}$ |
| PEG 30% | $10^{7.4}$ | $10^{5.9}$ | $10^{4.5}$ | n.d. | n.d. | $10^{2.9}$ | $\leq 10^{1.5}$ | $\leq 10^{1.5}$ |
| NH$_4$SCN 0.3 M | $10^{7.4}$ | $10^{5.5}$ | $10^{3.0}$ | $10^{2.6}$ | $\leq 10^{0.5}$ | $\leq 10^{0.5}$ | n.d. | n.d. | n.d. = not determined

From Table 2, it is clear that both agents alone have an apparent smaller virus inactivating effect on HIV-1 in comparison to the combination. Further, it is evident that the effect of the combination is a synergistic one, especially since the inactivation kinetics of the combination of polyether and chaotropic agent proceed substantially faster than the sum of the kinetics which are obtained by the individual agents.

It is to be understood that the description, specific examples and data, while indicating preferred embodiments, are given by way of illustration and exemplification and are not intended to limit the present invention. Various changes and modifications within the present invention will become apparent to the skilled artisan from the discussion and disclosure contained herein.

We claim:

1. A method for the production of a biological preparation, comprising
    (a) contacting a solution comprising a plasma protein with a polyether and a chaotropic agent to inactivate contaminating infectious agents by a physico-chemical or chemical treatment without the use of a detergent, and
    (b) removing the polyether and chaotropic agent to obtain the pharmaceutical preparation that is substantially free of infectious agents and denaturation products.

2. The method according to claim 1, wherein a polyhydroxyether is the polyether.

3. The method according to claim 2, wherein the polyhydroxyether is a polyalkylene glycol.

4. The method according to claim 3, wherein the polyalkylene glycol is a low molecular polyethylene glycol selected from the group consisting of PEG 200, PEG 300, PEG 400, PEG 600, PEG 900 and PEG 1000.

5. The method according to claim 1, wherein the inactivation of infectious agents is conducted in the presence of a polyether at a concentration of 5 to 30 percent by weight, wherein proteins are not precipitated.

6. The method according to claim 1, wherein the chaotropic agent is selected from the group consisting of thiocyanates, urea and guanidinium salts.

7. The method according to claim 6, wherein the chaotropic agent is a thiocyanate selected from the group consisting of ammonium thiocyanate, sodium thiocyanate and calcium thiocyanate.

8. The method according to claim 6, wherein the chaotropic agent is guanidinium hydrochloride.

9. The method according to claim 1, wherein the chaotropic agent is used at a concentration of 0.1 to 2M.

10. A method for producing virally-inactivated preparation containing a plasma protein, comprising:

(a) contacting the plasma protein with a polyether and a chaotropic agent to inactivate contaminating viruses without the use of a detergent, and (b) removing the polyether and chaotropic agent to obtain the virally-inactivated preparation, wherein the virally-inactivated preparation is substantially free of denatured forms of the plasma protein.

11. The method according to claim 10, wherein the polyether is a polyhydroxyether.

12. The method according to claim 11, wherein the polyhydroxyether is a polyalkylene glycol.

13. The method according to claim 12, wherein the polyalkylene glycol is a low molecular polyethylene glycol selected from the group consisting of PEG 200, PEG 300, PEG 400, PEG 600, PEG 900 and PEG 1000.

14. The method according to claim 10, wherein the polyether is at a concentration of 5 to 30 percent by weight, thereby avoiding the precipitation of proteins.

15. The method according to claim 10, wherein the chaotropic agent is selected from the group consisting of thiocyanates, urea and guanidinium salts.

16. The method according to claim 15, wherein the chaotropic agent is a thiocyanate selected from the group consisting of ammonium thiocyanate, sodium thiocyanate and calcium thiocyanate.

17. The method according to claim 15, wherein the chaotropic agent is guanidinium hydrochloride.

18. The method according to claim 10, wherein the chaotropic agent is used at a concentration of 0.1 to 2M.

19. The method according to claim 10, wherein the plasma protein is an immunoglobulin.

20. The method according to claim 10, wherein the plasma protein is selected from the group consisting of coagulation factors, fibrinolytic proteins and thrombolytic proteins.

21. The method according to claim 10, wherein the contacting occurs at a temperature of about 20° C. to about 60° C. over a period of about 1 hour to about 10 hours.

22. The method according to claim 10, wherein at least 80% of the activity level of the plasma protein is maintained in the virally-inactivated preparation.

23. The method according to claim 22, wherein at least 90% of the activity level of the plasma protein is maintained in the virally-inactivated preparation.

* * * * *

UNITED STATES PATENT AND TRADEMARK OFFICE
CERTIFICATE OF CORRECTION

PATENT NO. : 5,770,199
DATED : June 23, 1998
INVENTOR(S) : Johann Eibl, et. al.

It is certified that error appears in the above-identified patent and that said Letters Patent is hereby corrected as shown below:

Title page, delete item [22] PCT Filed: Jan. 10, 1995 and item [86] PCT No: PCT/IB95/00019, insert between item [21] Appl. No.: 624,516 and item [87] PCT Pub. No.: WO95/09657 the following:

--[22] PCT Filed: October 6, 1994--; and

--[86] PCT No. PCT/EP94/03298--.

Signed and Sealed this

Ninth Day of February, 1999

Attest:

*Acting Commissioner of Patents and Trademarks*

*Attesting Officer*